US012665065B2

(12) United States Patent
Tsoukalis

(10) Patent No.: US 12,665,065 B2
(45) Date of Patent: Jun. 23, 2026

(54) CLOSED LOOP PAIN MANAGEMENT INFUSION

(71) Applicant: Micrel Medical Devices S.A., Koropi (GR)

(72) Inventor: Achilleas Tsoukalis, Papagou (GR)

(73) Assignee: Micrel Medical Devices S.A., Koropi (GR)

( * ) Notice: Subject to any disclaimer, the term of this patent is extended or adjusted under 35 U.S.C. 154(b) by 79 days.

(21) Appl. No.: 18/346,676

(22) Filed: Jul. 3, 2023

(65) Prior Publication Data

US 2024/0013883 A1 Jan. 11, 2024

(30) Foreign Application Priority Data

Jul. 5, 2022 (EP) ..................................... 22183203

(51) Int. Cl.
| | |
|---|---|
| *G16H 20/17* | (2018.01) |
| *G16H 40/40* | (2018.01) |
| *G16H 50/20* | (2018.01) |
| *G16H 50/30* | (2018.01) |
| *H04L 67/125* | (2022.01) |

(Continued)

(52) U.S. Cl.
CPC ............. *G16H 20/17* (2018.01); *G16H 40/40* (2018.01); *G16H 50/20* (2018.01); *G16H 50/30* (2018.01); *H04L 67/125* (2013.01); *G16H 70/20* (2018.01); *G16H 70/40* (2018.01)

(58) Field of Classification Search
None
See application file for complete search history.

(56) References Cited

U.S. PATENT DOCUMENTS

| | | | |
|---|---|---|---|
| 11,367,519 B1 | 6/2022 | Heldman et al. | |
| 2017/0258986 A1* | 9/2017 | Tsoukalis | .......... A61M 5/14244 |

(Continued)

FOREIGN PATENT DOCUMENTS

| | | |
|---|---|---|
| EP | 3217304 A1 | 9/2017 |
| EP | 4039291 A1 | 2/2022 |
| WO | 2012128718 A1 | 9/2012 |

OTHER PUBLICATIONS

Althous et al, Postoperative Pain Trajectories and Pain Chronification—an Empirical Typology of Pain Patients, Pain Medicine 2018; 19: pp. 2536-2545 (Year: 2018).*

(Continued)

*Primary Examiner* — Gregory Lultschik
(74) *Attorney, Agent, or Firm* — Bookoff McAndrews, PLLC

(57) ABSTRACT

The invention refers to an apparatus for controlling a drug infusion pump. The drug is preferably a pain medication. The apparatus controls the infusion pump to apply an infusion protocol, wherein an infusion protocol defines times and amounts of drug infusion. A providing unit provides monitoring data of a patient during the application of an infusion protocol, wherein the monitoring data is indicative of an effect of the infused drug on the respective patient. A customized protocol determination unit determines a customized infusion protocol based on the currently applied infusion protocol and the monitoring data. A controlling unit controls the infusion pump to apply the customized infusion protocol instead of the currently applied protocol.

20 Claims, 3 Drawing Sheets

(51) Int. Cl.
   *G16H 70/20*          (2018.01)
   *G16H 70/40*          (2018.01)

(56)                    References Cited

U.S. PATENT DOCUMENTS

| | | | |
|---|---|---|---|
| 2019/0122764 A1 | 4/2019 | Handler | |
| 2019/0209779 A1* | 7/2019 | Osorio | .................. A61B 5/1118 |
| 2020/0246621 A1* | 8/2020 | Hofius | ................... G16H 40/67 |

OTHER PUBLICATIONS

Chapman et al, Improving Individual Measurement of Postoperative Pain: The Pain Trajectory, The Journal of Pain, vol. 12, No. 2, 2011: pp. 257-262 (Year: 2011).*

Kannampallil et al, Characterizing the pain score trajectories of hospitalized adult medical and surgical patients: a retrospective cohort study, Pain 2016, vol. 157, No. 12, 2739-2746 (Year: 2016).*

European Search Report issued on Nov. 8, 2023 in counterpart European Patent Application No. 23182996.1 (9 pages, in English).

* cited by examiner

CLOSED LOOP PAIN MANAGEMENT INFUSION

RELATED APPLICATIONS

This application claims priority to EP Patent Application No. 22183203.3, filed on Jul. 5, 2022, which is incorporated herein by reference in its entirety.

THE FIELD OF THE INVENTION

The invention refers to an apparatus, a method and a computer program product for controlling an automatic infusion pump configured for drug infusion into a patient. Moreover, the invention refers to an infusion pump comprising the apparatus.

BACKGROUND OF THE INVENTION

An infusion pump delivering opioids and other analgesics to relieve pain, infuses a combination of basal rate, e.g. continuous infusion, and bolus. The pump has a bolus handset, i.e. a handy switch that patient presses when he/she feels pain, and pump delivers a quantity of analgesic called bolus, given at high infusion rate; basal and bolus preprogrammed by physician. The process and pump are called PCA as Patient Controlled Analgesia. Delivery modes in PCA are basal rate, e.g. constant infusion, bolus, e.g. a patient demanded additional injection of drug, auto-bolus, e.g. a series of bolus at interval time, and combination of those. Per se, this is a pain control in which a patient controls additional drug delivery with bolus, however there is a need to modify initial protocol most of the cases and nurses are sent to a patient's home for this modification. So the first problem to solve is how to emulate nurse/doctor's corrections of the initial protocol automatically from the pump and avoid the cost and trouble of visits at home.

The second problem to solve is the stress of the doctors/ nurses on how to program the pump with correct protocol since there are hundreds of protocols depending on the therapy, the patient and the drug. It is impossible to remember all those protocols and errors in programming analgesia pumps are very often and patients feel pain or receive more analgesic than needed with other side effects, wherein physician cannot predict such outcomes accurately.

Thus, it would be advantageous if an automatic and reliable infusion pump could be provided that allows to take the individual needs of a patient into account.

BRIEF DESCRIPTION OF THE INVENTION

It is an object of the present invention to provide an apparatus, a method and a computer program, a further drug infusion pump comprising the apparatus that allow optimizing a drug management of a patient to increase patient comfort.

In a first aspect an apparatus is presented for controlling a drug infusion pump configured for drug infusion into a patient, wherein the drug is preferably a pain medication, wherein the apparatus controls the infusion pump to apply an infusion protocol, wherein an infusion protocol defines times and amounts of drug infusion, wherein the apparatus comprises a) a monitoring data providing unit for providing monitoring data of a patient during the application of an infusion protocol, wherein the monitoring data is indicative of an effect of the infused drug on the respective patient, b) a customized protocol determination unit for determining a customized infusion protocol based on the currently applied infusion protocol and the monitoring data, and c) a controlling unit for controlling the infusion pump to apply the customized infusion protocol instead of the currently applied protocol.

Since the customized infusion protocol is customized based on a currently applied infusion protocol and monitoring data, the infusion protocol can be adapted to an individual patient in an objective and secure manner. This allows to increase the comfort of the patient while it is still ensured that the drug infusion is still in a secure range. Moreover, the monitoring data allows for an objective assessment of a respective situation of the patient decreasing subjective influences on the drug management such that the drug management for a patient can be optimized. Thus, the apparatus allows for an optimization of the drug management of a patient to increase patient comfort.

The apparatus is configured for controlling a drug infusion pump configured for drug infusion into a patient. Generally, the apparatus can be realized in form of any software and/or hardware that is configured to perform the functions defined above. Moreover, the apparatus can be realized as integrated part of the infusion pump, for instance, integrated hardware and/or software in the infusion pump, but can also be realized as stand-alone software and/or hardware application that is communicatively coupled to the infusion pump. For example, the apparatus can be realized in form of a computer system acting a server that communicates with the infusion pump, for instance, via wireless or wired communication methods to control the drug infusion pump.

The drug infusion pump can be any drug infusion pump that allows to automatically infuse a predetermined amount of a drug into a system of the patient, in particular, into the bloodstream or into tissue near a nerve. The controlling of the drug infusion pump can be realized in any known manner, for instance, by sending respective signals to one or more hardware units of the drug infusion pump that can be utilized for the controlling of the infusion of the drug. For example, control signals can be send to a valve regulating the amount of a drug infused into a patient or to a miniature pump system with a motor speed control. The drug can generally be any drug that is utilized together with a drug infusion pump and administered continuously or regularly, in particular, without supervision of a physician or other professional. Preferably, the drug is a pain medication for regulating pain of a patient. The patient is preferably a human being, but can also be an animal.

The infusion pump is configured to apply an infusion protocol based on the controlling of the apparatus. An infusion protocol defines times and amounts of drug infusion to be applied to a patient. In particular, an infusion protocol comprises infusion parameters that determine these times and amounts of drug infusion. For example, an infusion parameter can be a basal infusion rate, an amount of drug infused during a bolus infusion, the frequency of a series of bolus called auto-bolus, an upper or lower limit of an infusion parameter, etc. A plurality of different infusion protocols exists depending on the respective therapy, utilized drug, or patient context. In most cases, a drug infusion protocol comprises a basal infusion rate that is to be applied continuously or bolus at predetermined time intervals, for instance, every minute or every ten minutes. The infusion protocol then defines the amount of drug that is infused in this way by the infusion pump and, if applicable, the timing of the infusion. Further, usually drug infusion pumps provide the possibility of a user-induced bolus infusion. In a user-induced bolus infusion the user indicates to the drug infusion pump, for instance, via a respective user interface, to apply an additional drug infusion, for example, in cases of a sudden episode of pain above the normal pain level. In such cases the infusion protocol defines the amount of drug infused into the patient during a bolus infusion and optionally also a waiting time before the allowance of the next user induced bolus infusion. Moreover, the infusion protocol can further define security margins for the drug infusion. For example, it is preferred that the infusion protocol defines hard and soft limits of drug infusion. Soft limits are thresholds for the amount of drug infusion that is set to trigger a warning to a patient or caregiver if the amount should be exceeded. However, soft limits can be overruled, for instance, by a respective caregiver, if the situation demands. Hard limits are generally set such that they cannot be overcome and are utilized to secure the patient from possible fatal side effects of the drug.

Further, it is preferred that the infusion protocol comprises a monitoring data protocol that determines the type and timing of the monitoring data that is to be determined during the application of the infusion protocol. Thus, the monitoring data protocol can be adapted to the respective situations in which a respective infusion protocol is applied. For example, if a specific infusion protocol is to be applied after a specific treatment, the monitoring data protocol can determine that the determining and providing of the monitoring data is only started after the first 12 hours due to this specific therapy, whereas for an infusion protocol applied to a chronic pain patient the monitoring data protocol can be set to directly start acquiring and providing respective monitoring data.

Preferably, the apparatus comprises a setup unit configured for determining a base infusion protocol based on therapy information during a setup of the infusion pump, wherein the base infusion protocol is applied to the patient as first infusion protocol after setup. In particular, the setup unit can have access to a storage unit on which a plurality of base infusion protocols are already stored that are associated with specific therapy information. A separate unit can then automatically determine a suitable base infusion protocol based on the therapy information. Additionally or alternatively user machine interaction process can be utilized in which the setup unit is configured for adjusting one or more suitable base infusion protocols to a professional such that the professional can select the to-be-applied base infusion protocol or confirm a suggested base infusion protocol. Thus, the drug infusion treatment can be started without a user like a professional having to manually define a respective infusion protocol, but respectively known and preferably clinically confirmed standard base infusion protocols can be utilized. Preferably, the therapy information comprises at least one of patient data, drug information and application context information. Patient data can refer to any data related to the patient. In particular, patient data comprise at least one of age, sex, weight, known intolerances, etc. The drug information can refer to any kind of information that allows to identify the one or more drugs to be infused by the infusion pump. For example, the drug information can refer to a name of the drug or any other unique identifier of the respective drug like concentration. The application context information can relate to any further information that could be utilized to select the most suitable drug infusion protocol for a patient. In particular, the application context information can comprise at least one of disease information, already applied therapy information, type of surgery, whether the disease is chronical or decreasing, current therapeutic state of a patient, etc.

Preferably, the base infusion protocol further comprises a monitoring data protocol determining the type and timing of the to-be-determined monitoring data, wherein the monitoring data providing unit is configured to apply the monitoring data protocol for providing the monitoring data. Providing a monitoring data protocol together with a base infusion protocol allows to provide each infusion protocol with a specific monitoring data protocol that is specifically adapted for the respective infusion protocol and is also specifically adapted to the respective therapy information. Thus, the monitoring data protocol can be specifically adapted from the beginning to the individual situation of the patients that is determined based on the therapy information. Utilizing a base infusion protocol optionally together with a monitoring data protocol, allows to start an infusion therapy directly with an infusion protocol that is adapted as much as possible to the individual situation of the patient such that the later performed amendments and customizations of the infusion protocol performed by the apparatus are as small as possible.

However, the apparatus can also be provided without utilizing a setup unit determining a base infusion protocol. For example, the apparatus can be configured to utilize a predetermined standard starting infusion protocol that is then adapted to the patient based on the monitoring data as described below. Alternatively, the apparatus can be configured to prompt a professional caregiver to provide a respective starting infusion protocol.

The monitoring data providing unit is configured for providing monitoring data of a patient during the application of an infusion protocol. In particular, the monitoring data providing unit can be realized as a data interface for interfacing with other computational units, in particular, with a user interface, a sensor or a database. However, the monitoring data providing unit can also be realized as a user interface, sensor or database itself. For example, the monitoring data providing unit can be configured for accessing a database on which the monitoring data is stored already. However, the monitoring data providing unit can also directly receive the monitoring data, for instance, form a sensor or a user interface. The monitoring data providing unit is then configured after receiving the monitoring data to provide the monitoring data, for instance, to the customized protocol determination unit.

The monitoring data is generally indicative of an effect of the infused drug on the respective patient. Preferably, the infused drug is a pain medication for relieving pain and the monitoring data is indicative of the pain relief caused in the respective patient. Moreover, in a preferred embodiment the monitoring data is also indicative of side effects of the infused drug on the respective patient. The monitoring data can be acquired, for instance, by a sensor sensing the effect of the respective infused drug on the respective patient. For example, a heartrate sensor can sense that after the application of the infused drug, for instance, a pain medication, a heartrate of the patient decreases due to decreased pain. Moreover, also other sensors can be utilized depending on the utilized drug. In particular, if the drug is a pain medication any kind of stress sensor can be utilized, for instance, blood pressure sensors, heartrate sensors, a cortisol sensors, $CO_2$ sensors determining sedation level, etc. that allows to determine pain induced stress.

Preferably, the monitoring data comprises pain monitoring data indicative of pain experienced by the patient and side-effect monitoring data indicative of occurring side effects. In a preferred embodiment the pain monitoring data includes a visual analogue scale (VAS) pain score. In particular, the VAS pain score can be determined by causing a patient to answer a respective standardized questionnaire. For example, the infusion pump or the apparatus can be provided with a respective user interface, like a monitor with a touchscreen or the like, that can provide the questionnaire at certain times to the patient and determine based on the answers the respective VAS pain score.

Additionally or alternatively the monitoring data can include the number and timing of patient induced bolus infusions. In particular, an increase in the amount of patient induced bolus infusions per time indicates an increase in pain of the patient. The side effect monitoring data can depend on the type of drug utilized in the infusion pump. For example, the infusion protocol can be configured to provide a respective information on possible side effects and which type of monitoring data for the side effects should be determined. For example, in case of pain medication, side effects can refer to a numbness or a motor block of one or more limbs of the patient. Also dizziness or nausea are common side effects of pain medication. In a preferred embodiment also in this case a respective questionnaire is utilized to determine a severity, for instance, in form of a score, of the respective side effects.

Generally, the type and timing of the to-be-determined monitoring data can be determined based on the monitoring data protocol. The monitoring data protocol can be predetermined, for instance, by a professional user like a physician doing a setup of the infusion pump. However, also a standard monitoring data protocol can be utilized that has shown to be suitable for most used cases. However in a preferred embodiment as already discussed above a base infusion protocol determined based on therapy data also comprises a respective monitoring data protocol.

A customized protocol determination unit is configured to determine a customized infusion protocol based on the currently applied infusion protocol and the monitoring data. In particular, predetermined rules and relations between the monitoring data and respective infusion protocol parameter can be utilized as part of a customizing algorithm to amend the currently applied infusion protocol based on the monitoring data. Generally, the utilized customizing algorithm can be predetermined for all cases, but can also be individual for each infusion protocol. For example, the infusion protocol can comprise information indicative of a respectively to be utilized customizing algorithm that determines how the infusion protocol, in particular, infusion protocol parameters, is to be customized based on respectively determined monitoring data. For example, the customizing algorithm can comprise coefficients that determine a relation between respective monitoring data and an infusion protocol parameter, wherein the infusion protocol can comprise information indicating the values to be set for these coefficients. Preferably, the customizing algorithm is a Proportional-Integral-Derivative (PID) type algorithm utilizing the monitoring data to determine the respective difference between a current state of the patient, e.g. patient is in pain, and a desired state, e.g. patient experiences no or a predetermined low amount of pain, wherein the coefficients of the different parts of the PID algorithm are provided by the infusion protocol or predetermined. In a preferred embodiment, the customized protocol determination unit is configured to determine the customized infusion protocol further based on historical data comprising a plurality of historical infusion protocols of respective patients and corresponding monitoring data. For example, the historical data can be utilized by searching the historical data, by the customized protocol determination unit, based on a similarity measure to find similar patient cases and to customize the infusion protocol based on the selected similar patient cases. Preferably, the customized protocol determination unit is configured to utilize a machine learning based pain management model for determining the customized infusion protocol based on a currently utilized infusion protocol and the monitoring data, wherein the machine learn based pain management model has been trained based on the historical data to determine a customized infusion protocol based on the currently utilized infusion protocol and monitoring data of different pumps and patients. The machine learning based pain management model can be for instance, a neural network, support vector regression, a decision tree, a regression algorithm, or any other algorithm that can be trained based on historical datasets. A respective machine learning model can be trained utilizing any known training method based on historical data of a plurality of patients comprising respective monitoring data and customized infusion protocols. The such trained machine learning based pain management model can then be stored and the apparatus can be configured to access the storage for utilizing the model to determine the customized infusion protocol utilizing the machine learning based pain management model by inputting the respective monitoring data to the model.

The controlling unit is then configured to control the infusing pump to apply the customized infusion protocol instead of the currently applied protocol. In particular, the control unit can automatically provide the respective signal to the infusion pump together with the details of the infusion protocol. However, the controlling unit can also be configured to provide the customized infusion protocol first to a professional user for conformation. After respective confirmation has been received the confirmed customized infusion protocol can then be applied by the infusion pump to the patient.

In an embodiment, the apparatus further comprises an iteration control unit configured for controlling to continuously or regularly a) provide monitoring data during the application of an infusion protocol, b) determining a new customized infusion protocol based on the currently applied infusion protocol and the monitoring data and c) controlling the infusion pump to apply the new customized infusion protocol. In particular the controlling to continuously or regularly perform the steps a), b) and c) described above can be regarded as a closed loop control of the infusion pump. In particular, the iteration allows to adjust the customized infusion protocol to the individual needs of a patient not only after the setup of the infusion pump but continuously or regularly as long as the therapy is necessary. For example, patients experience pain, in particular, chronic pain, differently and different developments of their pain can be possible. For example, in some cases the pain might slowly increase over time, or the pain will increase in some episodes and decrease in others. Performing a respective iteration by the iteration control unit allows to adjust the customized infusion protocol so that such developments are taken into account, for instance, increasing the infusion rate for phases of increased pain but decreasing the infusion rate again for phases of decreased pain. Thus, the closed loop control of the apparatus allows for even more comfort for a patient.

In an embodiment, the monitoring data comprises pain monitoring data including a VAS pain-score and wherein the customized infusion protocol is determined by amending a currently applied infusion protocol based on the VAS pain score. Preferably, the customizing of the infusion protocol comprises increasing the drug infusion if an increase of the VAS pain score above a predetermined threshold is determined. In particular, it is preferred that the customized infusion protocol is determined by increasing an infusion rate, and optionally a user induced bolus volume, by a percentage value determined by the difference between the VAS pain score provided by the monitoring data and a predetermined threshold pain score. Moreover, it is preferred that the customized infusion protocol is determined by a differential term defined by the difference between a previously determined and a current VAS score. Thus, developments in the VAS score can be taken into account.

In an embodiment, the monitoring data comprises side effect monitoring data, wherein the customized infusion protocol is determined by decreasing an infusion rate, and optionally a user induced bolus volume, if the side effect monitoring data indicates an increase or appearance in one or more predetermined side effects. In a preferred embodiment the monitoring data refers to a result of a questionnaire indicating whether the patient is experiencing numbness or a motor block in one or more limbs. If the patient is experiencing at least one of these side effects the infusion rate is preferable decreased by a predetermined amount or proportionally in case of quantifying response of numbness or motor block questions. However, also other side effects can be taken into account. For example the side effect monitoring data can also refer to the onset of side effects like nausea, dizziness, sleepiness, etc. The decreasing of the infusion rate can for instance, depend on the respective side effect. For example, the occurrence of some predetermined side effects can lead to the decreasing of the infusion rate then the occurrence of other predetermined side effects. Preferably, a user specific prioritization of predetermined side effects can determine the decreasing of the infusion rate. For example, the apparatus can cause a user to indicate which side effects that can occur are acceptable for a user and which are experienced as life quality decreasing by the user, i.e. the patient. The infusion rate can then be decreased based on this priority list decreasing the infusion rate more if side effects occur that are quality decreasing for the user and less if side effects occur that are acceptable for the user.

In an embodiment, the utilized infusion protocol follows a pain decay curve, wherein the determining of a customized infusion protocol further comprises determining a customized pain decay curve based on the monitoring data. Generally, a pain decay curve describes how pain, for instance, caused by an injury or surgical procedure, decays with time. Thus, the infusion protocol can take this decay into account by decreasing an amount of infused pain medication based on the pain decay curve. For example, the infusion protocol can follow a base pain decay curve that is considered as generally applicable for the respective case. However, it has been shown that patients experience the pain and pain decay differently and thus follow different pain decay curves, wherein it is often not possible to predict upfront which pain decay curve a patient will follow. Thus, customizing the pain decay curve based on the monitoring data allows to even more individualize the pain management for a respective patient.

Preferably, determining a customized pain decay curve comprises selecting from a plurality of predefined pain decay curves the customized pain decay curve based on the monitoring data. In particular, medical studies have shown that patients tend to follow one of four possible pain decay curves, wherein it is often not possible to predict upfront which pain decay curve a patient will follow. Thus, the selecting can be a selecting from the four determined pain decay curves based on the monitoring data. For example, during setup a base infusion protocol can follow a standard pain decay curve, for instance, a pain decay curve with a middle value of decay with time. Based on the monitoring data it can then be determined whether a specific patient follows a lower pain decay curve, for instance, if a patient often utilizes a bolus infusion, or a faster pain decay curve for instance, if a patient does not utilize a bolus infusion but indicates one or more side effects. Thus, the comfort of the patient can be improved also in cases of decaying pain.

In a further aspect of the invention, an infusion pump is presented configured for automatic drug infusion in a patient comprising an apparatus according to any of the preceding claims controlling the drug infusion of the infusion pump.

In the further aspect of invention, a computer-implemented method is presented for controlling a drug infusion pump configured for drug infusion into a patient, wherein the method controls the infusion pump to apply an infusion protocol, wherein an infusion protocol defines times and amounts of drug infusion, wherein the method comprises a) providing monitoring data of a patient during the application of an infusion protocol, wherein the monitoring data is indicative of an effect of the infused drug on the respective patient, b) determining a customized infusion protocol based on the currently applied infusion protocol and the monitoring data, and c) controlling the infusion pump to apply the customized infusion protocol instead of the currently applied protocol.

In the further aspect of invention, a computer program product is presented for controlling a drug infusion pump, wherein the computer program product is configured for causing an apparatus as described above to perform the method as described above.

In a further aspect of the invention an infusion pump is presented that has a dedicated to its functions drug library (database) installed, with fields of therapy, profile, drug and protocol, characterized by having pre-installed therapy structure and values for all protocols for infusion, and where pump infusion mode and infusion closed loop infusion control algorithm or AI parameters or coefficients are selected automatically by the pump once a therapy and drug are selected while profile further selects a generic experts proven protocol for patient or therapy specificities (profile).

In an embodiment, the pump is internally and automatically adjusting infusion protocol during infusion and till end, according to patient feedback and therapy specifics like pain decay function.

In an embodiment, at first few hours an adjustment of the generic expert protocol to a patient specific is calculated using patient feedback as input for adjustment and pre-installed algorithm or AI coefficients, while after this, steady state pain line, and pain decay curves are transformed (calculated) to infusion parameters steady or decay values in time to be applied in the running infusion.

In an embodiment, in case of decaying pain, first a mean of all available curves is applied, and then according to patient feedback, a higher or lower curve is selected to be followed as infusion progress in time.

In an embodiment, in non-decaying pain, according to patient feedback, higher or lower protocol infusion parameters set is calculated by linear or non-linear regression not exceeding high infusion limits of the drug library.

In an embodiment, patient feedback means are one or more of bolus given/time, bolus demands/time, pain scale from 0-10, numbness, motor block, where algorithm has an internal output of pain intensity negative or positive so with negative infusion protocol parameters need to be lowered and with positive to be increased and how much (coefficient or percentage).

In an embodiment, linear or non-linear regression or AI coefficients are determined first by a clinical trial, and then from a continuously improving effectiveness system with collected by a remote server from pumps running historic data, evaluating efficiency of the algorithms and recalculating coefficients for further download to pumps for improvement.

It shall be understood that the method as described above, the apparatus as described above and the computer program product as described above have similar and/or identical preferred embodiments, in particular, as defined in the dependent claims.

It shall be understood that a preferred embodiment of the present invention can also be any combination of the dependent claims or above embodiments with the respective independent claim.

These and other aspects of the present invention will be apparent from and elucidated with reference to the embodiments described hereinafter.

DETAILED DESCRIPTION OF EMBODIMENTS

Figure 1:
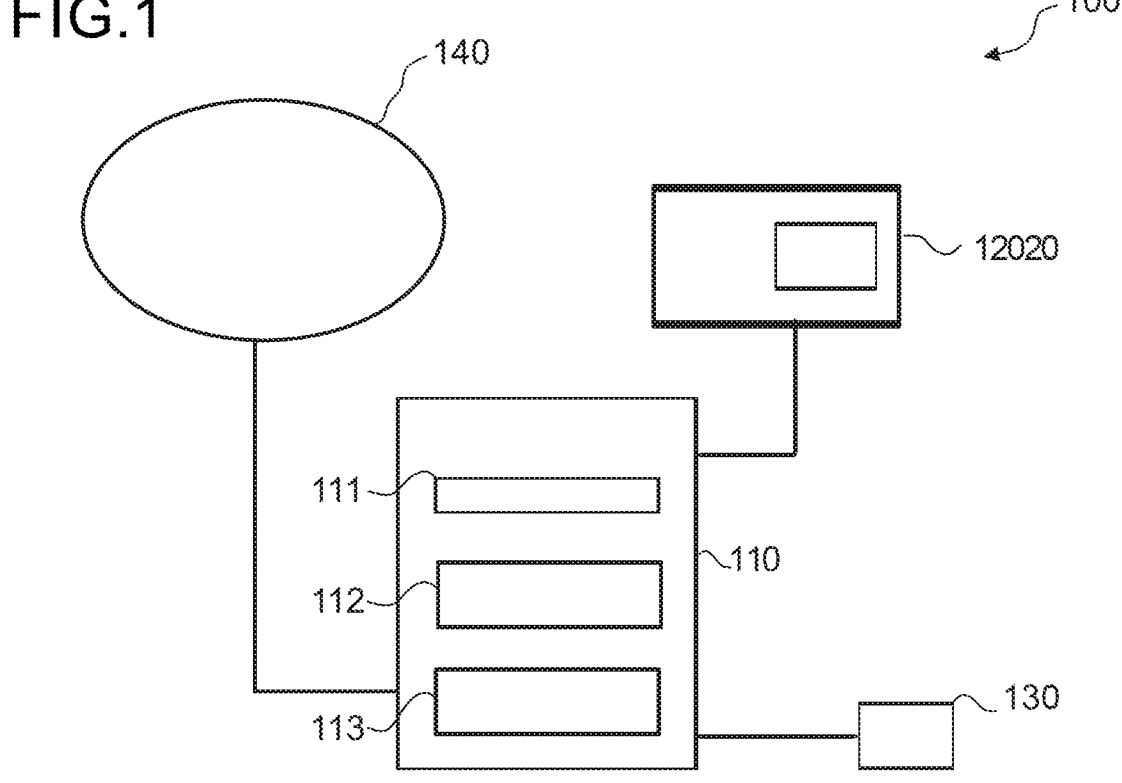
FIG. 1 shows schematically and exemplarily an embodiment of an apparatus for controlling an infusion pump.

The standard way pain is treated with PCA pumps today leaves a patient on his/her own and only a nurse visit at home can help him/her if he/she adjusts infusion parameters according to history record in the pump of how often the bolus button has been pressed. This is a problem to be solved as a doctor can understand the pain of a patient, by questioning the patient, and monitoring in pump historic how many times he pressed the bolus button. In EP4039291 A1 a remote monitoring system is described that informs caregivers about VAS pain score as the patient answers question on the pump to estimate a pain on the scale of 0-10 additionally to the bolus button, and other questions as motor block, numbness etc. providing information to the caregiver.

However, in this case no real closed loop infusion is described, since a nurse has to go and reprogram the pump after interpretation of the patient pain and other symptoms feedback.

There are several indications where pain relief is helped by analgesic PCA infusion, like terminal cancer usually a category called palliative care with IV infusions, or post-operative pain, or obstetric pain with Peripheral Nerve Block, Epidural, or Labor.

In palliative care the source of pain is constant and treatment is constant too. In such a case, the below described invention of a closed loop infusion that is modifying, i.e. customizing, an infusion protocol and not only using just the bolus function can adjust the infusion protocol relatively quickly and follow up in time with the treatment, with slight automatic protocol modifications.

In post-operative care pain is usually treated with regional analgesia. The pain is decreasing to zero after 3 to 7 days after operation. Therefore, the invention as described below allows with a closed loop infusion to follow the constant change of pain with a constant change of the infusion protocol to follow the decay of the pain and reduce the amount of analgesic infused and so every side effect, while optimizing pain relief of patient.

Generally, doctors and nurses are usually not experts in pump programming, as it is hard to find in literature initial protocol values for a given patient and how the protocol values vary with therapy and delivery route. The result is that in most of the cases patients feel pain or have other side effects. Although PCA is aimed to be patient controlled analgesia, bolus injection volume and basal rate as well as auto-bolus frequency, need adjustment. In the invention as described below this is done by the pump itself leading to a real closed loop system.

Today, a patient feels pain first and then presses a bolus button for the infusion of a predefined bolus of pain medication. Then the pain disappears for some time and then reappears again such that the patient again presses the button or even worse still feels pain after bolus infusion and needs more bolus infusions. In the present invention, pressing a bolus button means patient discomfort and the apparatus can control the pump to automatically give additional auto-bolus or to increase a basal rate of infusion depending on the therapy, i.e. infusion protocol, so that the patient stops feeling pain. However, for feedback the apparatus utilizing the closed loop algorithm in the present invention can not only use the average time between patient induced bolus infusion but also other monitoring data like a VAS score and other provided by the patient.

It is thus the aim of the present invention to provide an infusion pump that provided infusion protocols customized internally by a respective algorithm that may also include artificial intelligence, using as input patient feedback on the outcome effects of a pain medication, for instance, answers to questions like pain he feels on a pain scale, motor block, numbness etc.

As described in EP4039291 A1 an infusion protocol can be selected based on information on a therapy, patient profile, and drug. A drug library database can be filled with base infusion protocols with literature-based knowledge from clinical trials associated with respective information on the application cases for the respective protocol. This reduces the stress of a caregiver to find what is the best protocol for the case. For doing this, therapy and patient profile information can be used in a way to select the best protocol. In particular, the patient profile can comprise patient characteristics like age (adult/child or average weight) and in some cases as in a peripheral nerve block therapy, the patient profile can describe the surgery type like total knee arthroplasty, or sciatic surgery or in labor therapy the patient profile can comprise a woman's height.

Moreover, the base infusion protocol can also comprise information if a decay in pain is expected and to be taken into consideration or if pain is constant. Moreover, the base infusion protocol can also comprise a monitoring protocol, for instance, indicating, which questions to ask for the determination of the monitoring data and the calculation of the adjustment of the infusion protocol.

Drug libraries of pumps in the prior art are often empty as each Hospital has its own that is provided to the library of the pumps of the hospital. Ambulatory pumps of prior art do the same. The inconvenience is that in the ambulatory world, caregivers must work with and use protocols of different origin that are not the same, and most of the time caregivers do not know what protocol to program. Thus, in most cases the caregivers rely on the patient induced bolus function to take care of not optimally provided protocols and worse do not even know how to adjust correctly the current infusion protocol, when the patient feels pain or has a motor block.

FIG. 1 shows schematically and exemplarily a system 100 comprising an apparatus for controlling an infusion pump 110, a database 140, an infusion pump 120 and one or more sensors 130. The infusion pump can comprise a display on which respective instructions or questions can be displayed to a patient or caregiver. The database, herein also called drug library, can be realized as any database system and comprises base infusion protocols stored associated with therapy information such that based on respective therapy information a suitable base infusion protocol can be selected, for instance, by a setup unit of the apparatus 110. The sensor 130 can be any sensor providing monitoring data indicative of pain of a patient, for example, a heart rate sensor, a CO2 sensor, a blood pressure sensor, etc. However, in some embodiments the sensor and the database can be omitted, for example, if the first utilized infusion protocol is defined by a caregiver or if the monitoring data is only based on respective questions answered by a patient.

The apparatus 110 and the infusion pump 120 can be separate systems that are communicatively coupled, as shown in FIG. 1, in particular, if the apparatus is realized as a cloud service. However, the apparatus 110 and the infusion pump can also be integrated, in particular, the apparatus can be realized as software causing a respective computer hardware of the infusion pump to carry out the functions of the apparatus as defined by its units.

The apparatus 110 is configured for controlling the drug infusion pump 120 to apply an infusion protocol to a patient. The apparatus 110 comprises a monitoring data providing unit 111, a customizing protocol determining unit 112 and a controlling unit 113. The monitoring data providing unit 111 is configured for providing monitoring data of a patient during the application of an infusion protocol. For example, the monitoring data providing unit 111 can receive the monitoring data from the sensor 130 and/or the infusion pump 120. In a preferred embodiment, the infusion pump provides as monitoring data answers to questions with respect to the effect of the drug medication and/or the amount of user induced bolus to the monitoring data providing unit 111. The monitoring data providing unit 111 can then provide the monitoring data to the customizing protocol determining unit 112, e.g. can be realized as a data interface. The monitoring data is indicative of an effect of the infused drug on the respective patient.

The customized protocol determination unit 112 is then configured for determining a customized infusion protocol based on the currently applied infusion protocol and the monitoring data, as will be described in more detail in the following. The controlling unit 113 is then configured for controlling the infusion pump 120 to apply the customized infusion protocol instead of the currently applied protocol.

Figure 2:
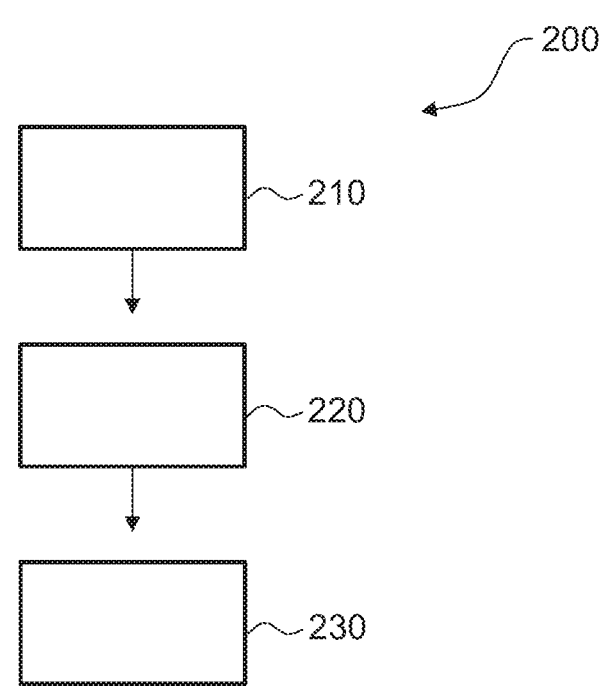
FIG. 2 shows schematically and exemplarily a flowchart of an embodiment of a method for controlling an infusion pump.

FIG. 2 shows schematically and exemplarily a flow chart of a computer-implemented method 200 for controlling a drug infusion pump configured for drug infusion into a patient. In particular, the method can be performed by an apparatus as described in FIG. 1. The method comprises in a first step 210 providing monitoring data of a patient during the application of an infusion protocol, wherein the monitoring data is indicative of an effect of the infused drug on the respective patient. In a further step 220 a customized infusion protocol is determined based on the currently applied infusion protocol and the monitoring data. Then in step 230 the infusion pump is controlled to apply the customized infusion protocol instead of the currently applied protocol.

Further details and preferred embodiments of the invention are described in the following. In the present invention it is preferred to provide an infusion pump with pre-installed expert groups published and clinically tested initial (generic) protocol values for each therapy/profile/drug as base infusion protocols so that at the start of an infusion therapy the protocol is already adjusted to the patient as best as possible.

Further, a preferred embodiment the input from patient answers to questions, or bolus demand/bolus given data is used as monitoring data of a closed loop algorithm, to adjust automatically the protocol during infusion as a closed loop analgesia. Thus, the pump is configured for automatic adjustment, increasing patient satisfaction and comfort, outcome and reducing costs of treatment. Preferably, the pump comprises a drug library with filled-in base infusion protocols so that an infusion protocol with a suitable algorithm for the closed loop control of infusion can be utilized, for instance, comprising a pain decay or respective rules and algorithms for the protocol parameter adjustment. These are visible and not visible to the user parameters of the infusion protocol that are used by the pump. Those infusion protocol parameters can comprise an indication of decaying or not decaying pain, specific to the to-be-adjusted parameters of the infusion protocol, questions to be provided to a patient for determining the monitoring data and when to ask them. The closed loop control may run in the pump after patient feedback or/and at determined time window. Since the pump can be a connected device, and can communicate with a remote server, information on protocol customizations and patient feedback adjustment can be sent to the server. Thus, a caregiver can control and monitor the progress of the pain management. Moreover, historical data provided by a plurality of pumps for a plurality of patients comprising infusion protocols and respective therapy outcomes, can be utilized. For example, a machine learning based pain model can be trained based on the respective historical data. The model can then be utilized for adjusting the infusion protocol and/or respective rules and algorithms for determining the infusion protocol based on the monitoring data. Preferably after a review process by manufacturer experts such adjustments can be downloaded back to all pumps so to constantly improve the system.

Preferably, the present invention provides a pump that first has pre-installed expert group protocols for each therapy/profile/drug and then allows a physician the choice to have just a suggestion on a protocol modification. For example, the suggestion can be provided on the pump, e.g. a display, on the course of the infusion or on a remote server. Preferably, the pump is an internet of things device with remote communication and monitoring of infusion protocols. However, preferably, it can also be chosen to utilize a full closed loop internal protocol modification. Therefore, preferably the pump provides a user with the option to just give an advice to a caregiver or do the pain management adjustment in a closed loop infusion. Preferably, the customizing of the infusion protocol comprises adjusting an infusion basal rate, if present, a bolus volume, refractory time, bolus infusion rate, auto bolus frequency and/or auto bolus volume.

Preferably, each infusion protocol is associated with information on whether the pain therapy is palliative, post-operative, obstetric, which delivery route is utilized, e.g. IV, intrathecal, peripheral nerve block, epidural. Thus, the infusion protocol is available and can be selected for different situations. Thus, based on the respectively selected infusion protocol the closed loop algorithm can customize the protocol parameters that are associated with the infusion protocol.

Generally, the infusion pump can provide a plurality of infusion modes, like basal rate i.e. a constant infusion rate, basal rate together with bolus infusion, i.e. a constant rate and a bolus generated by patient demand, for instance, based on a bolus button pressed, auto bolus i.e. a number of bolus infused without patient intervention, and combinations therefrom.

Generally, the invention is about an infusion pump with automatic self-adjustment of its applied infusion parameters as closed loop analgesia. The pump can have a body, a power source that can be a battery, a controller, display and communications means such as WiFi, GSM, RFID communicating with a distant server as an IoT device transceiving data from the utilized infusion but also from the customized infusion parameters, a memory, wherein preferably, a part of the memory comprises a database drug library. The controller can be regarded as comprising or being part of the apparatus for controlling the infusion pump. The apparatus comprises a customized infusion protocol determination unit that can utilize a respective algorithm or machine learning based pain model that determines a customized infusion protocol according to respective input parameters, in particular, monitoring data. Preferably, the pump comprises a setup unit with a pre-installed a drug library database, comprising base infusion protocols associated with information on therapy variants, patient profile variants, and/or drug variants and is configured to select and/or suggest a base infusion protocol if provided with respective information. Preferably, the base infusion protocol includes a suggested infusion mode and values for the infusion parameters of the infusion mode, such as basal rate, bolus volume and rate, bolus refractory time, auto bolus frequency and volume, etc. Further the base infusion protocol defines soft and hard limits for the respective parameters, wherein soft means that the limit can be exceeded with a warning and hard cannot be exceeded. Moreover, it is preferred that the base infusion protocol comprises the rules and algorithm to be utilized for customizing the respective base infusion protocol. For example, closed loop coefficients like a rate of change coefficient, a pain decay curve, etc. All parameters and coefficients of a base infusion protocol can also be altered by a caregiver and/or a patient, but can preferably not be erased as default values that can be readjusted when needed. Moreover, it is preferred that the base infusion protocol comprises a monitoring protocol specifying when, how and which monitoring data is to be acquired. For examples, questions can be provided to be displayed to the patient, e.g. on the pump or connected devices, wherein the result of the questions can then be used as monitoring data to customize the base infusion protocol. The pump can be programmed also with other custom questions per patient that are not used in the closed loop algorithm but valuable in therapy monitoring.

Figure 3:
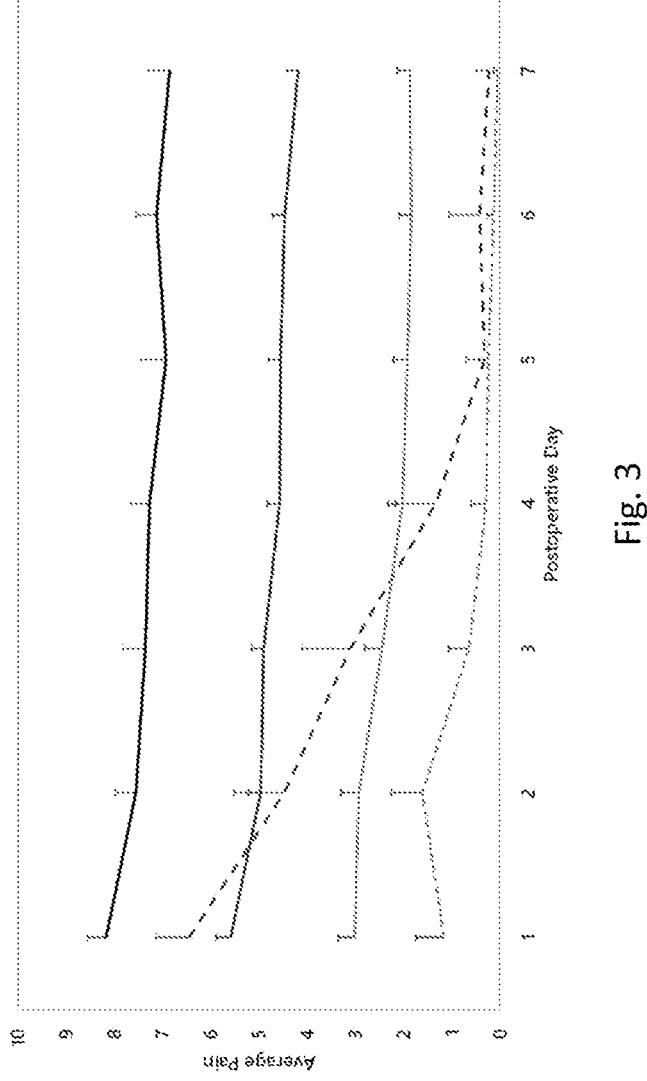
FIG. 3 shows schematically and exemplarily possible post-operative pain trajectory curves.

The present invention provides a pump that utilizes a closed loop algorithm for self-adjusting infusion parameters while respecting safety limits as defined by the base infusion protocol applied. In particular, if the closed loop algorithm calculates higher parameter values than a respectively defined limit, the control unit is configured to ignore the determined parameter values and to only infuse the defined limit value so that the hard limit is never exceeded. The treatment of pain has several variants, in IV infusions for palliative care, pain is constant, and treatment is long for months, while in post-operative pain, pain is decaying following so called pain decay curves as shown in FIG. 3 and ends after a few days. In post-operative pain it is common to use regional analgesia, wherein a catheter is provided near a nerve of the operation site. In this case a common side effect of pain medication is a motor block or numbness of a limb. It is therefore preferred that the monitoring data also comprises side effect data, for instance, asks a patient questions about side effects. In post-operative analgesia also in some cases pain is only at mobilization and not at rest, so special questions for rest and mobilization can be asked. In IV infusions more drug can increase a $CO_2$ level in the body leading to the patient looking bluish. Thus, in such an infusion protocol the monitoring data can comprise a $CO_2$ monitoring as an input parameter to the algorithm to reduce infusion rate if the $CO_2$ level exceeds predetermined limits. However, in some infusion protocols for palliative care, also high $CO_2$ levels can be acceptable for pain treatment or provide no high risk for the health of the patient.

Preferably, the infusion pump allows for a user to choose between using a closed loop or open loop classic PCA treatment or a closed loop with final decision to accept or modify algorithm proposals from a caregiver on the pump or remotely.

Providing questions to a patient and basing the customizing of the infusion protocol on the answers as monitoring data input to the customization algorithm is advantageous over only utilizing information on bolus on demand infusions. In particular, it can be shown that bolus demand is not an accurate pain level indicator, such that in medical practice usually the VAS score is used as the standard. Thus, it is preferred that in post-operative/peripheral nerve block pain therapies, the monitoring data is acquired based on questions indicating the VAS score at rest and at mobilization. It is thus preferred for this application that the customization infusion protocol determination unit is configured to determine a customized infusion basal rate based on the VAS score at rest and a patient induced bolus quantity adjusted by the VAS score at mobilization. When a patient moves and feels pain he/she demands a bolus infusion. Moreover, additionally to adjust a basal rate of infusion, it is further preferred that the monitoring data is used for adjusting the bolus quantity. It is preferred that in an embodiment, that the infusion protocol comprises as part of the monitoring protocol specific questions that are used as therapy feedback and input in the customization algorithm, wherein the question can be indicative of at least one of a VAS score in general analgesia like IV, a VAS score and Numbness/motor block at rest and VAS score and Numbness/motor block at mobilization in Peripheral Nerve Block cases. For example, respective questions can be very simple, like in the form of "Numbness at rest Y/N" etc.

Preferably, the base infusion protocol defined infusion values that are defined and published by expert groups for an infusion setup and that are associated, for instance, with a specific patient profile. This allows for an automatic quick adjustment in the first hours of treatment by the customization algorithm, since it is very likely that the generic base infusion protocol parameters are not too far away from the individually needed infusion parameters. Moreover, it has been found that for decaying pain and non-decaying pain the same or very similar infusion protocols can be utilized for the first few hours of infusion, wherein a fine adjustment of the infusion protocol to the actual patient and his actual needs is preferably performed in that phase in which decaying and non-decaying pain have the same appearance. Thus, a respective monitoring data protocol can be provided that indicates the acquisition of the monitoring data in particular in this phase. However, it has been shown for the case of post-operative pain, that it is not advisable to change infusion parameters within the first 12 hours as patient will always feel pain and is often not able to answer the questions correctly or even an adjustment will not lead to a decrease of the pain. Thus, in such cases the base infusion protocol can provide a monitoring protocol that causes a monitoring data acquisition only after the first 12 hours, wherein for the first 12 hours either the base infusion protocol parameters or parameters amended and controlled by a physician are utilized. To select the right base infusion protocol the protocols can be associated with respective therapy information such as Pain IV or Pain IV, adult, weight in pediatric or height in child delivery. Moreover, even details on the therapy can be associated for an even finer selection, like for peripheral nerve block as therapy the type can be specified, like total knee arthroplasty or sciatic surgery.

The customizing algorithm to customize the infusion parameters of the infusion protocol according to patient feedback provided by the monitoring data can be based on several options, for example, it can be preferably a linear regression algorithms that associates the infusion protocol parameters with the respective monitoring data. However, also PID algorithms, neural networks, etc. can be utilized after a respective clinical trials to ensure the security of the algorithm in respective application cases. Generally, an infusion protocol can comprise a basal rate infusion and or a bolus infusion. In case that in a protocol there is no basal rate or bolus the algorithm does not calculate a respective adjustment of the basal rate or bolus. Preferably, the infusion protocol comprises an indication if the pain is expected to follow a pain decaying curve and further which monitoring data is to be used in the customizing algorithm, for example, which questions to ask when and how to use the results in the algorithm. Preferably, the infusion parameters and/or coefficients in the customizing algorithm, for instance, proportional constants, etc. are continuously or at predetermined times amended to the best values in use determined by further clinical experience or preferably by a machine learning based pain model. Preferably, the infusion pumps are all connected to a remote server, such that a machine learning based pain model, for instance, a remote neural network, can continuously learn from the provided historical data of therapies in use. The machine learning pain model can then be used for determining a customized therapy, but also for proposing new dependencies between the monitoring data and the respective protocol parameters, for instance, in form of amended algorithm coefficients. These amendments of the customizing algorithms can then be uploaded to the databases of the infusion pumps from time to time. Since sometimes also a caregiver might see the need to set coefficients of a customizing algorithm, these coefficients can be provided as part of a configuration pump menu and can be changed based on clinical trials or on practice.

For example, if a coefficient K determines a rate of change of a parameter, for instance, an infusion parameter, it is known that if K is too high, i.e. the rate of change can be high in one step, the system can oscillate and not find a steady state level. In medical practice it is preferred to avoid such a situation in which infusion parameters oscillate too much around the optimal value. It has been found that in medical applications it is therefore preferred to not allow for a change rate that is more than 20% of the previously used parameter value. Moreover, it is known that pain is subjective and some patients feel a lot of pain independent of the dosing of a pain medication or there are other options to reduce the pain than analgesic infusion. Thus, respective limits of the change rate allow to take this into account such that a patient does not dose the medication too much in one step, but also tries possible other options. Further, it is preferred to determine a lower pain limit that is acceptable for the patient. Such a lower pain limit can also be subjective but in medical practice it has shown that acceptable pain lies about a VAS score of 3. Thus, it is preferred that the customizing algorithm is configured to not customize an infusion protocol if a VAS score pain of less than 3 is determined. However, this lower limit can also be adjusted, for instance, based on the patient or a caregiver.

In the following some preferred examples for customizing algorithms are described in more detail. First in the following a preferred relation utilized by the customizing algorithm for converting bolus demand data to a VAS score is described. In some application cases, like in terminal cancer therapy, it is not advisable or even possible to ask the patient about his/her pain. However, in most cases the patient still has the possibility, for instance, to press a button for a patient induced bolus infusion. In this context a bolus demanded time interval (BT) can be defined as a mean time between at least the last two, preferably, a predetermined number greater than two, asked bolus demands. Moreover, in most infusion protocols further a refractory time is defined, wherein a patient induced bolus has not been given if asked within the refractory time, i.e. the refractory time is the allowed minimum time between two patient induced bolus infusions. In the following example the refractory time (RT) can be arbitrarily set, i.e. can be set based on the respective infusion protocol. In a preferred utilized algorithm for determining a VAS score (PSVAS) form the bolus demand a further coefficient is utilized referring to the ratio coefficient (RC). This leads to the preferred transformation equation $$PSVAS = RT * \frac{RC}{BT}.$$

The coefficient RC can be set based on the respective therapy case and can be provided, for example, by the base infusion protocol. However, the coefficient RC can also be set based on the experience of a caregiver, or can be learned by a machine learning pain model based on respective historical cases. Preferably, the coefficient RC does not exceed the limit of 10. In the following an example is provided with RC=3 and RT=30 min. For this exemplary case the transformation equation leads to the following relation between the bolus demanded time interval (BT) and the VAS score.

| BT | VAS |
| --- | --- |
| 3 | 30 |
| 5 | 18 |
| 10 | 9 |
| 20 | 4.5 |
| 30 | 3 |
| 40 | 2.25 |
| 50 | 1.8 |
| 60 | 1.5 |
| 90 | 1 |
| 120 | 0.75 |
| 160 | 0.5625 |

Additionally or alternatively, such a relation can also be determined in a clinical trial for each application case or can be learned by a machine learning pain model based on respective historical data.

In the following a preferred customizing algorithm for determining based on monitoring data the infusion parameters is described. It is proposed that in particular a linear regression algorithm can be useful for determining based on a VAS score or bolus demand, optionally converted to a VAS score, respective infusion parameters to adjust a currently utilized infusion protocol, for instance, a base infusion protocol, from generic to a specific patient in order to increase patient comfort and reduce the frequency of patient induced bolus asked. A linear regression algorithm generally comprises one or more coefficients that are determined by the respective application case. For example, the coefficients of the linear regression can be defined in a clinical trial for respective decaying and non-decaying pain therapies. These coefficients can also be altered by caregivers if they want to experiment on better patient outcomes. However, also in this case it is preferred that the infusion protocol provides upper limits for each patient type that cannot be exceeded. Preferably, the customizing algorithm can exceed predetermined soft limits, however, then utilizes a specifically for this case defined change reduction algorithm such that the hard limit is not reached, if possible.

In a preferred linear regression algorithm an acceptable VAS score level is predefined, for example, a pain VAS score of 3 or 2 is considered as being acceptable. In this case for VAS scores below the acceptable pain score, here for a pain score of 2,1,0, the algorithm is configured to incrementally reduce the infusion parameters, for example, the amount of infused pain medication or the rate of infusion of the pain medication. For a pain score equal to the acceptable pain score the algorithm does not change the currently used infusion parameters. For all other cases the infusion parameters are increased. The predefined acceptable pain is defined in the following as the Pain Offset (PO). Preferably, in this case further a change coefficient (CC) is defined as the coefficient that determines the percentage change of the infusion parameters based on the pain score. Also this coefficient can be predetermined based on experience, clinical trials or learned by a machine learning based pain model based on historical data and can be provided for each application case by the base infusion protocol. Thus, the customizing algorithm preferably used the linear regression equation $$\text{Change } \% = (VAS - PO) * CC$$

An example, of the results of this algorithm for an exemplarily chosen CC=4 and PO=2 are

| VAS | Change % |
| --- | --- |
| 0 | −8 |
| 1 | −4 |
| 2 | 0 |
| 3 | 4 |
| 4 | 8 |
| 5 | 12 |
| 6 | 16 |
| 7 | 20 |
| 8 | 24 |
| 9 | 28 |
| 10 | 32 |

Generally, both the coefficient CC and the acceptable pain PO can be adjusted by a caregiver, for instance, in a configuration menu. However, also default values determined by clinical trials can be provided by a database, preferably, by a base infusion protocol and can be upgraded by a pump upgrade, if necessary. Also these default parameters may change based on a machine learning based pain model utilizing big data collected from a plurality of patients and pumps from a remote server to learn respective optimal coefficients for respective application cases.

In the above case the change rate is proportional to the VAS score, and thus the pain experienced by the patient. In other applications the change rate can also be determined based on other monitoring data, e.g. pain indicators. For example, instead of the VAS score, the change rate can also be determined proportional to the difference of the last two VAS scores. Moreover, also other CC coefficients can be utilized. Further also a PO can be omitted.

Preferably, the customizing algorithm is a PID algorithm, i.e. a Proportional-Integral-Derivative type algorithm. In particular, in such a PID algorithm the rate of change is determined based on a proportional change plus an integral change plus a differential change. The proportional change can be realized utilizing the second equation, described above. In a preferred embodiment the differential part is determined utilizing, for example, the last two VAS scores determined for a patient, e.g. VAS1-VAS2. Thus, the differential part does not depend on an acceptable pain level. The coefficients of the PID algorithm, like the CC described in the equation two above, can be predetermined by clinical trials, experience of a caregiver, or can be learned by a machine learning algorithm. These coefficients can then be provided, for example, as part of a base infusion protocol for a respective patient case, i.e. based on respective therapy information.

Alternatively, to the above equation, a respective machine learning based model can be utilized that has been trained based on historical data. In this case it is preferred that the machine learning based pain model, e.g. a neural network, used as inputs a series of monitoring data, for instance, the last 5 VAS score values, and further a series of previous outputs, e.g. change rates. This allows the model to be trained such that a history of infusion and pain is taken into account to avoid oscillations and allow for a faster stabilization.

In another preferred embodiment, there is a second stage when calculated a percentage of change for cases in which a currently applied dose is close to a soft or hard limit For example, in this case a non-linear filter can be applied to the result of the rate of change calculation. This leads to an asymptotical approach to the respective limit, preferably to the hard limit, wherein the rate of change, i.e. change % is reduced the closer the infusion parameter comes to the respective limit. In particular, a function with a horizontal asymptote can be applied or a respective watch table can be utilized for amending the rate of change determined, for instance, as described above. Moreover, it is preferred that a general stability threshold is provided that cannot be exceeded by a rate of change. For example, the stability limit can be set to 20% of the currently utilized infusion parameter. This allows to avoid strong oscillations of the infusion parameters values around an optimal value.

In a preferred embodiment, the two above equations are utilized by a customizing algorithm as follows. First monitoring data is acquired, for example, questions are asked at predetermined time intervals, usually every 4 hours. In case of steady pain, for instance, in palliative care, it is preferred that a monitoring protocol indicates that the VAS score is determined based on a bolus demand conversion. In particular in this case the patients are often elderly and/or weak and cannot easily respond to questions. Accordingly, the above transformation equation can be utilized to convert a bolus demand into a VAS score. However, if the patient is able to respond to questions it is preferred that the respective result of the questionnaire is used for determining the VAS score and directly use the such determined VAS score. Moreover, also both options can be combined for an even more accurate determination of the VAS score. For example, the VAS score determined based on the bolus demand and the VAS score form the questionnaire can be compared and a mean value can be determined. Based on the such determined VAS score the second equation can then be utilized for customizing the infusion protocol.

In case of steady pain that is mostly experienced at mobilization, it is preferred that an infusion protocol is provided that defined a patient induced bolus only or only comprises a very low basal infusion rate. Also in this case the above equations together with respective monitoring data configured to the pain at mobilization can be utilized to adjust the infusion parameters, in particular the bolus parameters.

The case of decaying pain is mostly occurring in a post-operative application using a regional analgesia. In this case it has been found that the pain follows one of the pain decay curves shown in FIG. 3, wherein most frequently occurring case is the dotted line of a fast decaying pain. In the other cases the pain is reduced more slowly. In regional analgesia, a catheter is put close to a nerve, and for therapy reasons a patient often needs to move even if he/she feels pain. Pain at mobilization is different than at rest. Preferably, the infusion protocol for this case comprises a basal infusion rate to treat the pain at rest, and a patient induced bolus to deal with the pain at mobilization. To determine a pain decay curve to be applied to a patient, a questionnaire can be provided to determine if a patient is mostly young and active or elderly and more inactive, since it has been found that this can have an influence on the respective pain decay curve followed by the individual patient. Generally, the decay of pain according to medical practice starts after 12-24 hours after surgery and then follows one of the pain decal curves shown in FIG. 3.

Preferably, for this application the following monitoring data is acquired, a VAS score at rest, a VAS score at mobilization, the occurrence of motor block after bolus infusion, the occurrence of numbness after bolus infusion. Based on this monitoring data, the first information, i.e. the VAS score at rest is utilized in the second equation to customize a basal infusion rate. The second information, i.e. the VAS score at mobilization, is utilized in the second equation customize the patient induced bolus, wherein the VAS score can also be determined based on the bolus demand during mobilization. The third information, i.e. the presence of a motor block, is utilized to reduce the bolus parameters by a predetermined percentage and also the basal rate by a predetermined percentage. The fourth information, i.e. the occurrence of numbness, is then also used to reduce bolus parameters by a predetermined percentage and the basal rate by a predetermined percentage as a preferred option. Optionally also quantitative numbness or motor block questions can be provided to a user, wherein the quantitative result can then be used in the customizing algorithm. Preferably, the customizing algorithm then decreased the infusion parameters proportional to the quantitative result. The respective percentages for the reduction can be different for all case and depend on respective clinical trials, user preferences, expert knowledge, etc.

In surgery cases, with a pain decay curve it is preferred that for a VAS score that is equal or below a pain offset (PO) value, for example, 3 or 2, the second equation is utilized with increased CC to reduce infusion rates more rapidly to follow the decay function. Also a table with respective values to reduce a basal rate or bolus parameter not linearly can be used. For example the rate of change can be 5% in case of VAS=0, 10% in case of VAS=−1 and 20% in case of VAS=−2 to follow a decaying pain function.

Generally, after the initial adjustment of the infusion protocol, i.e. of the infusion parameters of the protocol, from generic to the specific patient, in the first hours of infusion, the pump can be configured to gradually reduce the infusion parameters of the protocol according to the pain decay curve so that the patient does not receive more drug than needed, and to reduce side effects of the analgesics such as motor block and numbness, nausea etc. A decaying infusion parameter equation can also be applied instead or in combination with a pain decay curve.

Clinical evidence shows that analgesics in surplus in the body even locally are not desirable even dangerous as published in several publications. Opioids are addictive, and their volume in treatments should be the lowest possible. It is the aim of the present invention not only to reduce steady state i.e. constant-pain drugs but also decaying-pain drugs.

The application and calculation for customized infusion parameters is preferably done as seldom as possible for stability reasons. For example, a new customizing can be triggered based on a new or differing answer to a monitoring questions, or only after predetermined times defined by the monitoring protocol, for example, after several refractory time windows when there are accumulated bolus demands.

Moreover, it is preferred that for safety and stability reasons, an independent safety check is performed, for example by a safety unit of the pump or apparatus. For example the safety unit can receives the change rate proposed by the customizing algorithm, and determine if the rate of change is within the stability limit, e.g. below 20%. Further, the safety unit can adjust the rate of change to be within the hard limits described in the infusion protocol or can provide a warning if a soft limit is exceeded. Moreover, the safety unit can be adapted send respective control data i.e. input and output data to a server for confirmation or as historical data for a machine learning process.

Other variations to the disclosed embodiments can be understood and effected by those skilled in the art in practicing the claimed invention, from a study of the drawings, the disclosure, and the appended claims.

For the processes and methods disclosed herein, the operations performed in the processes and methods may be implemented in differing order. Furthermore, the outlined operations are only provided as examples, and some of the operations may be optional, combined into fewer steps and operations, supplemented with further operations, or expanded into additional operations without detracting from the essence of the disclosed embodiments.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the providing of monitoring data, the determining of the customized infusion protocol, the controlling of the infusion pump, etc. performed by one or several units or devices can be performed by any other number of units or devices. These procedures can be implemented as program code means of a computer program and/or as dedicated hardware.

A computer program product may be stored/distributed on a suitable medium, such as an optical storage medium or a solid-state medium, supplied together with or as part of other hardware, but may also be distributed in other forms, such as via the Internet or other wired or wireless telecommunication systems.

Any units described herein may be processing units that are part of a classical computing system. Processing units may include a general-purpose processor and may also include a field programmable gate array (FPGA), an application specific integrated circuit (ASIC), or any other specialized circuit. Any memory may be a physical system memory, which may be volatile, non-volatile, or some combination of the two. The term "memory" may include any computer-readable storage media such as a non-volatile mass storage. If the computing system is distributed, the processing and/or memory capability may be distributed as well. The computing system may include multiple structures as "executable components". The term "executable component" is a structure well understood in the field of computing as being a structure that can be software, hardware, or a combination thereof. For instance, when implemented in software, one of ordinary skill in the art would understand that the structure of an executable component may include software objects, routines, methods, and so forth, that may be executed on the computing system. This may include both an executable component in the heap of a computing system, or on computer-readable storage media. The structure of the executable component may exist on a computer-readable medium such that, when interpreted by one or more processors of a computing system, e.g., by a processor thread, the computing system is caused to perform a function. Such structure may be computer readable directly by the processors, for instance, as is the case if the executable component were binary, or it may be structured to be interpretable and/or compiled, for instance, whether in a single stage or in multiple stages, so as to generate such binary that is directly interpretable by the processors. In other instances, structures may be hard coded or hard wired logic gates, that are implemented exclusively or near-exclusively in hardware, such as within a field programmable gate array (FPGA), an application specific integrated circuit (ASIC), or any other specialized circuit. Accordingly, the term "executable component" is a term for a structure that is well understood by those of ordinary skill in the art of computing, whether implemented in software, hardware, or a combination. Any embodiments herein are described with reference to acts that are performed by one or more processing units of the computing system. If such acts are implemented in software, one or more processors direct the operation of the computing system in response to having executed computer-executable instructions that constitute an executable component. Computing system may also contain communication channels that allow the computing system to communicate with other computing systems over, for example, network. A "network" is defined as one or more data links that enable the transport of electronic data between computing systems and/or modules and/or other electronic devices. When information is transferred or provided over a network or another communications connection, for example, either hardwired, wireless, or a combination of hardwired or wireless, to a computing system, the computing system properly views the connection as a transmission medium. Transmission media can include a network and/or data links which can be used to carry desired program code means in the form of computer-executable instructions or data structures and which can be accessed by a general-purpose or special-purpose computing system or combinations. While not all computing systems require a user interface, in some embodiments, the computing system includes a user interface system for use in interfacing with a user. User interfaces act as input or output mechanism to users for instance via displays.

Those skilled in the art will appreciate that at least parts of the invention may be practiced in network computing environments with many types of computing system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, datacenters, wearables, such as glasses, and the like. The invention may also be practiced in distributed system environments where local and remote computing system, which are linked, for example, either by hardwired data links, wireless data links, or by a combination of hardwired and wireless data links, through a network, both perform tasks. In a distributed system environment, program modules may be located in both local and remote memory storage devices.

Those skilled in the art will also appreciate that at least parts of the invention may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources, e.g., networks, servers, storage, applications, and services. The definition of "cloud computing" is not limited to any of the other numerous advantages that can be obtained from such a model when deployed. The computing systems of the figures include various components or functional blocks that may implement the various embodiments disclosed herein as explained. The various components or functional blocks may be implemented on a local computing system or may be implemented on a distributed computing system that includes elements resident in the cloud or that implement aspects of cloud computing. The various components or functional blocks may be implemented as software, hardware, or a combination of software and hardware. The computing systems shown in the figures may include more or less than the components illustrated in the figures and some of the components may be combined as circumstances warrant.

Any reference signs in the claims should not be construed as limiting the scope.

The invention refers to an apparatus for controlling a drug infusion pump. The drug is preferably a pain medication. The apparatus controls the infusion pump to apply an infusion protocol, wherein an infusion protocol defines times and amounts of drug infusion. A providing unit provides monitoring data of a patient during the application of an infusion protocol, wherein the monitoring data is indicative of an effect of the infused drug on the respective patient. A customized protocol determination unit determines a customized infusion protocol based on the currently applied infusion protocol and the monitoring data. A controlling unit controls the infusion pump to apply the customized infusion protocol instead of the currently applied protocol.

The invention claimed is:

1. An apparatus for controlling a drug infusion pump configured for drug infusion of a drug into a patient, wherein the apparatus controls the infusion pump to apply an infusion protocol, wherein the applied infusion protocol defines times and amounts of drug infusion, wherein the apparatus comprises:

a monitoring data providing unit for providing monitoring data of a patient during an application of an infusion protocol, wherein the monitoring data providing unit includes one or more processors, wherein the monitoring data is indicative of an effect of the infused drug on the patient, wherein the monitoring data comprises pain monitoring data including a visual analogue scale (VAS) pain-score and/or a bolus demand, a customized protocol determination unit for determining a customized infusion protocol based on the applied infusion protocol and the monitoring data, wherein the customized protocol determination unit includes one or more processors, wherein the customized infusion protocol is determined by amending a currently applied infusion protocol based on the VAS pain-score and/or the bolus demand, and a controlling unit for controlling the infusion pump to apply the customized infusion protocol instead of the applied infusion protocol, wherein the controlling unit includes one or more processors, wherein the customized infusion protocol is determined by amending an infusion rate by a change percentage, wherein the change percentage is based on a linear regression algorithm, wherein the change percentage is equal to a change coefficient multiplied by a difference in i) the VAS pain-score or the bolus demand converted to a VAS pain-score and ii) a predefined acceptable pain threshold.

2. The apparatus according to claim 1, further comprising an iteration control unit configured to continuously or regularly a) provide monitoring data during the application of an infusion protocol, b) determine a new customized infusion protocol based on the applied infusion protocol and the monitoring data and c) control the infusion pump to apply the new customized infusion protocol, wherein the iteration control unit includes one or more processors.

3. The apparatus according to claim 1, wherein the monitoring data comprises pain monitoring data indicative of pain experienced by the patient and side effect monitoring data indicative of occurring side effects.

4. The apparatus according to claim 1, wherein the customized infusion protocol is determined by increasing one or both of an infusion rate and a user induced bolus volume, by the change percentage determined by a positive difference between the VAS pain-score provided by the monitoring data and a predetermined threshold pain score.

5. The apparatus according to claim 1, wherein the monitoring data includes side effect monitoring data, wherein the customized infusion protocol is further determined by decreasing one or both of an infusion rate and a user induced bolus volume, if the side effect monitoring data indicates an increase or appearance in one or more predetermined side effects.

6. The apparatus according to claim 1, wherein the customized protocol determination unit further determines a customized pain decay curve based on the monitoring data.

7. The apparatus according to claim 6, wherein determining the customized pain decay curve comprises selecting the customized pain decay curve from a plurality of predefined pain decay curves, based on the monitoring data.

8. The apparatus according to claim 1, wherein the customized protocol determination unit is configured to determine the customized infusion protocol based on historical data comprising a plurality of historical infusion protocols of the patient and corresponding monitoring data.

9. The apparatus according to claim 8, wherein the customized protocol determination unit is configured to determine the customized infusion protocol based on a currently utilized infusion protocol and the monitoring data.

10. The apparatus according to claim 1, further comprising a setup unit for determining a base infusion protocol based on therapy information during a setup of the infusion pump, wherein the base infusion protocol is applied to the patient as a first infusion protocol after setup, wherein the setup unit includes one or more processors.

11. The apparatus according to claim 10, wherein the base infusion protocol further comprises a monitoring data protocol, the monitoring data protocol determining a type and timing of a determined monitoring data, wherein the monitoring data providing unit is configured to apply the monitoring data protocol for providing the monitoring data.

12. An infusion pump configured for automatic drug infusion in a patient comprising an apparatus according to claim 1.

13. A computer-implemented method for controlling a drug infusion pump configured for drug infusion into a patient, wherein the method controls the infusion pump to apply an infusion protocol, wherein the infusion protocol defines times and amounts of drug infusion, wherein the method comprises:

providing monitoring data of a patient during an application of an infusion protocol, wherein the monitoring data is indicative of an effect of the infused drug on the respective patient, wherein the monitoring data comprises pain monitoring data including a visual analogue scale (VAS) pain-score and/or a bolus demand, determining a customized infusion protocol based on the applied infusion protocol and the monitoring data, wherein the customized infusion protocol is determined by amending a currently applied infusion protocol based on the VAS pain-score and/or the bolus demand, and controlling the infusion pump to apply the customized infusion protocol instead of the applied protocol, wherein the customized infusion protocol is determined by amending an infusion rate by a change percentage, wherein the change percentage is based on a linear regression algorithm, wherein the change percentage is equal to a change coefficient multiplied by a difference in i) the VAS pain-score or the bolus demand converted to a VAS pain-score and ii) a predefined acceptable pain threshold.

14. The method according to claim 13, further comprising an iteration control unit configured to continuously or regularly a) provide monitoring data during the application of an infusion protocol, b) determine a new customized infusion protocol based on the applied infusion protocol and the monitoring data and c) control the infusion pump to apply the new customized infusion protocol, wherein the iteration control unit includes one or more processors.

15. The method according to claim 13, wherein the monitoring data comprises pain monitoring data indicative of pain experienced by the patient and side effect monitoring data indicative of occurring side effects.

16. The method according to claim 13, wherein the customized infusion protocol is determined by increasing one or both of an infusion rate and a user induced bolus volume, by the change percentage determined by a positive difference between the VAS pain-score provided by the monitoring data and a predetermined threshold pain score.

17. A non-transitory computer-readable medium storing instructions that, when executed by one or more processors, cause the one or more processors to perform computer-implemented method for controlling a drug infusion pump configured for drug infusion into a patient, wherein the method controls the infusion pump to apply an infusion protocol, wherein the infusion protocol defines times and amounts of drug infusion, wherein the method comprises, the method comprising:

provide monitoring data of a patient during an application of an infusion protocol, wherein the monitoring data is indicative of an effect of the infused drug on the respective patient, wherein the monitoring data comprises pain monitoring data including a visual analogue scale (VAS) pain-score and/or a bolus demand, determining a customized infusion protocol based on the applied infusion protocol and the monitoring data, wherein the customized infusion protocol is determined by amending a currently applied infusion protocol based on the VAS pain-score and/or the bolus demand, and controlling the infusion pump to apply the customized infusion protocol instead of the applied protocol, wherein the customized infusion protocol is determined by amending an infusion rate by a change percentage, wherein the change percentage is based on a linear regression algorithm, wherein the change percentage is equal to a change coefficient multiplied by a difference in i) the VAS pain-score or the bolus demand converted to a VAS pain-score and ii) a predefined acceptable pain threshold.

18. The medium according to claim 17, further comprising an iteration control unit configured to continuously or regularly a) provide monitoring data during the application of an infusion protocol, b) determine a new customized infusion protocol based on the applied infusion protocol and the monitoring data and c) control the infusion pump to apply the new customized infusion protocol, wherein the iteration control unit includes one or more processors.

19. The medium according to claim 17, wherein the monitoring data comprises pain monitoring data indicative of pain experienced by the patient and side effect monitoring data indicative of occurring side effects.

20. The medium according to claim 17, wherein the customized infusion protocol is determined by increasing one or both of an infusion rate and a user induced bolus volume, by the change percentage determined by a positive difference between the VAS pain-score provided by the monitoring data and a predetermined threshold pain score.

* * * * *